(12) United States Patent
Hateley et al.

(10) Patent No.: US 7,368,600 B2
(45) Date of Patent: May 6, 2008

(54) METHOD FOR PRODUCTION OF METHIONINE FROM HOMOSERINE

(75) Inventors: Martin Hateley, Aschaffenburg (DE); Christoph Kobler, Alzenau (DE); Christoph Weckbecker, Gründau-Lieblos (DE); Thomas Häussner, Bad Orb (DE); Jürgen Bilz, Freigericht (DE); Klaus Huthmacher, Gelnhausen (DE)

(73) Assignee: Degussa GmbH, Düsseldorf (DE)

( * ) Notice: Subject to any disclaimer, the term of this patent is extended or adjusted under 35 U.S.C. 154(b) by 0 days.

(21) Appl. No.: 11/657,534

(22) Filed: Jan. 25, 2007

(65) Prior Publication Data
US 2007/0190622 A1 Aug. 16, 2007

(30) Foreign Application Priority Data
Jan. 28, 2006 (DE) ...................... 10 2006 004 063

(51) Int. Cl.
*C07C 321/00* (2006.01)
*C07C 323/00* (2006.01)
*C07C 381/00* (2006.01)

(52) U.S. Cl. ..................................... 562/559

(58) Field of Classification Search ................. 562/559
See application file for complete search history.

(56) References Cited

U.S. PATENT DOCUMENTS

| 2,397,628 | A | 4/1946 | Snyder et al. |
| 3,189,526 | A | 6/1965 | Kinoshita et al. |
| 3,598,701 | A | 8/1971 | Tanaka et al. |
| 5,072,052 | A | 12/1991 | Boeck et al. |
| 5,770,769 | A | 6/1998 | Geiger et al. |
| 5,990,349 | A | 11/1999 | Geiger et al. |
| 6,303,348 | B1 | 10/2001 | Livshits et al. |
| 6,887,691 | B2 | 5/2005 | Livshits et al. |
| 6,960,455 | B2 | 11/2005 | Livshits et al. |
| 2002/0155556 | A1 | 10/2002 | Imaizumi et al. |
| 2005/0260721 | A1 | 11/2005 | Kroger et al. |

FOREIGN PATENT DOCUMENTS

CA 2548964 6/2005

OTHER PUBLICATIONS

Son, et al., "Stereochemical Mechanism of Iodoacetic Acid Mediated Decomposition of L-Methionine to L-Homoserine Lactone," *J. Am. Chem. Soc.*, 111 (4): 1363-1367.

*Primary Examiner*—Yvonne Eyler
*Assistant Examiner*—Jennifer Y Cho
(74) *Attorney, Agent, or Firm*—Michael A. Sanzo; Law Office of Michael A. Sanzo, LLC

(57) ABSTRACT

The invention relates to a method for production of D- and/or L-methionine via D- and/or L-homoserine with subsequent chemical transformation to give methionine.

20 Claims, No Drawings

METHOD FOR PRODUCTION OF METHIONINE FROM HOMOSERINE

CROSS REFERENCE TO RELATED APPLICATIONS

The present application claims priority to German application no. 10 2006 004 063.5, filed on Jan. 28, 2006. The contents of this prior application is hereby incorporated by reference in its entirety.

The present invention relates to the production of methionine by combination of biotechnological and chemical steps.

In particular, the present invention relates to the production of L-homoserine by fermentation and subsequent chemical conversion to L-methionine in one or more steps.

The amino acid methionine is currently produced industrially in large amounts worldwide and is of considerable commercial importance.

Methionine is employed in many fields such as, for example, pharmaceutical, health and fitness products. In particular, however, methionine is used as feed additive in many feeds for various farm animals, both the racemic form and also the enantiomerically pure form of methionine being able to be used.

On an industrial scale, methionine is produced chemically via the Bucherer-Bergs reaction, which is a variant of Strecker synthesis. In this method the starting substances methylmercaptopropionaldehyde (produced from acrolein and methylmercaptan), prussic acid, ammonia and carbon dioxide are reacted to form 5-(2-methylmercaptoethyl)hydantoin(methioninehydantoin), this is subsequently hydrolysed under alkaline conditions to give alkali metal methioninate and then the methionine is liberated by neutralization with acid, for example sulphuric acid or carbonic acid. Various other methods can also be used for producing methionine, such as, for example the amidocarbonylation reaction, the hydrolysis of proteins or fermentation.

Since methionine is produced industrially on a large scale, it is desirable to have an economic but also environmentally friendly process available.

Both Strecker synthesis and the Bucherer-Bergs reaction have the disadvantage that the poisonous precursors prussic acid and acrolein are used as $C_1$- and $C_3$-building blocks, respectively. Prussic acid is produced from methane and ammonia at high temperatures. Acrolein is produced by partial oxidation of propene which in turn is produced from petroleum. The methionine process is described in more detail, for example, in EP 1256571. The process for producing acrolein is described in more detail, for example, in EP 417723. Both processes are associated with high equipment usage and high energy requirement.

Owing to the price increase of petroleum in recent years, acrolein is also becoming increasingly more expensive and thus as a building block has become less and less attractive economically. Furthermore, not only prussic acid but also acrolein, because of their toxicity and physical properties with respect to safety and environmental protection, give rise to corresponding expenditure in the handling of large amounts.

Methionine is produced in chemical synthesis as a racemic mixture of D and L enantiomers. This racemate can be used directly as feed additive, since under in vivo conditions, there is a conversion mechanism which converts the unnatural D enantiomer into the natural L enantiomer. However, this conversion is associated with a loss of methionine and thus also a loss of bioefficiency compared with the same amount of pure L enantiomer. Therefore, more racemic D,L-methionine is required compared with L-methionine, to achieve the same effect.

It was therefore desirable to provide a process for production of methionine which is as far as possible of greater economic interest and more environmentally friendly and safer. In particular, it was desirable to provide a process for production of enantiomerically enriched L-methionine, very particularly preferably of as far as possible enantiomerically pure L-methionine, which should be able to be carried out on an industrial scale.

Previous processes which are based on the production of L-methionine using microorganisms as described, for example in WO04/024933, have the disadvantage that comparatively small yields are achieved. This has its origin, in particular, in the problems with the strictly organized regulatory network of microbial L-methionine biosynthesis, with the excretion of methionine from the cell into the fermentation broth, and also with the energy-intensive eight-electron step in the reduction of sulphate to hydrogen sulphide. Secondly, the limited solubility of methionine in water or in aqueous fermentation broths has the effect that methionine precipitates out at high biosynthesis performance in the fermentation and thus makes purification difficult. The complex purification leads as a result to the fact that considerable waste streams are produced, the removal of which is associated with high costs.

Although in WO05/059155 a method is described for the improved isolation of L-methionine from fermentation broths, the improvement is achieved, however, by a comparatively complicated sequence of steps which comprises, heating and dissolving the L-methionine in the fermentation broth, filtering off the biomass at a defined temperature and post-treating the methionine-containing biomass which was filtered off, concentrating the mother liquor by evaporation, cooling, crystallizing, filtering off, washing and drying the L-methionine from the mother liquor and recycling mother liquors, and by the fact that two different product streams are produced, namely a low concentration and a high-concentration L-methionine product. The forced production of two different methionine quality grades means, however, again increased expenditure and is moreover undesirable from the marketing point of view.

The said problems ultimately lead to a lower overall yield for a purely fermentative L-methionine method compared with the fermentative production methods of, for example, L-lysine, which have already been used for many years in industry and/or to a corresponding additional expenditure in the production of L-methionine by fermentation.

Against the background of the disadvantages of the prior art, it was, in particular, the object to provide a method for methionine which overcomes the above disadvantages described in more detail of the method of the prior art. This method should, as far as possible proceeding from another available precursor and producible by fermentation, lead in the simplest possible manner and without the use of the abovementioned hazardous chemicals to L-, D- or D,L-methionine, but preferably to L-methionine and in so doing overcome in particular the disadvantages of the conventional chemical methods and also of the direct biotechnological production methods for methionine.

It was a further object to provide a production method which can be carried out at least in part starting from natural or renewable raw materials.

A third object was to provide a method which can be carried out technically without problem, which makes L-methionine accessible in suitable amounts and purities.

These objects and also further objects which are not mentioned explicitly, but which can be derived or concluded from the context discussed herein without problem, are achieved in that another amino acid which is available and producible better by fermentation is used as starting material, which is then converted via a suitable chemical transformation without using the abovementioned hazardous chemicals to L-, D- or D,L-methionine, but in particular to L-methionine. By this means, not only the disadvantages of the conventional chemical production processes for methionine are overcome, but also those of the conventional production processes for L-methionine by direct fermentation. The amino acid homoserine has proved suitable according to the invention, which, in contrast to methionine, has a high water solubility and which is also accessible via fermentative methods.

The pathway described by Livak, Britton, VanderWeele and Murray ("Synthesis of dl-methionine", Journal of the American Chemical Society, (1945), 67, 2218-20) in which D,L-homoserine occurs as synthesis intermediate, proceeds first from D,L-2-amino-4-butyrolactone which leads via D,L-homoserine, N-carbamoylhomoserine, 4-(2-bromomethyl)hydantoin and 4-(2-methylthioethyl)-hydantoin, finally to D,L-methionine:

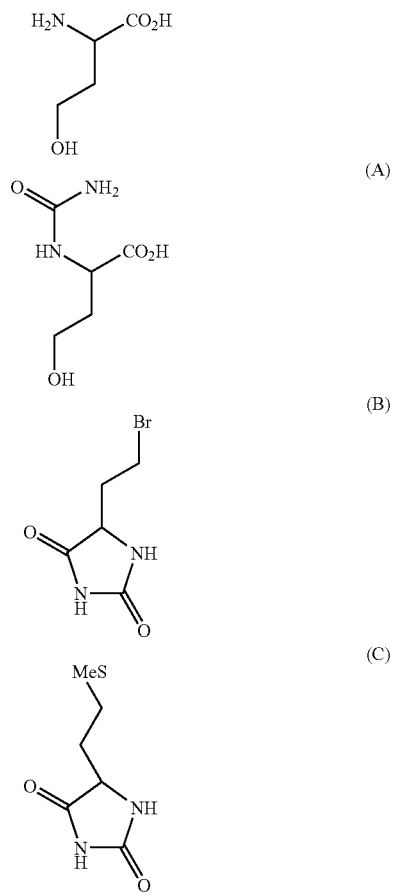

The deuterated homoserine derivatives HO—CHD-CH₂—CH(HNCOOtBu)COOtBu or H₃CC₆H₄SO₂O—CHD-CH₂—CH—(HNCOOtBu)COOtBu (tBu=tert-butyl) were used according to Son and Woodard ("Stereochemical mechanism of iodoacetic acid mediated decomposition of L-methionine to L-homoserine lactone", Journal of the American Chemical Society (1989), 111(4), 1363-7) as precursors of L-homoserine correspondingly deuterated in the 4 position. The corresponding non-deuterated compounds HO—CH₂—CH₂—CH(HNCOOtBu)COOtBu or H₃CC₆H₄SO₂O—CH₂—CH₂—CH(HNCOOtBu)COOtBu have not been described on the pathway to homoserine.

The subsequently schematized compounds 3,6-di(2-hydroxy-ethyl)-2,5-diketopiperazine, 3,6-di(2-chloroethyl)-2,5-diketopiperazine or 3,6-di(2-methylthioethyl)-2,5-diketopiperazine are chemical intermediates through which the pathway to D,L-methionine passes according to U.S. Pat. No. 2,397,628, however, starting not from homoserine, but starting from 2-acetyl-4-butyrolactone:

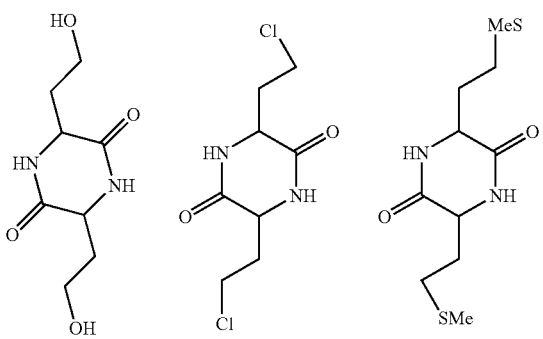

In addition there are further production methods for D,L-methionine which likewise do not start from homoserine, but start, for example, from 2-acetyl-4-butyrolactone via 2-amino-4-butyrolactone or appropriately protected 2-amino-4-butyrolactone, according to Snyder, Andreen, John, Cannon and Peters ("Convenient synthesis of dl-methionine", Journal of the American Chemical Society (1942), 64, 2082-4).

The synthesis according to Plieninger starts from 2-amino-4-butyrolactone ("Die Aufspaltung des γ-Butyrolactons und α-Amino-γ-butyrolactons mit Natriummethylmercaptid bzw. -selenid. Eine Synthese des Methionins" [The Cleavage of γ-Butyrolactone and α-Amino-γ-butyrolactone using Sodium Methyl Mercaptide or Selenide. A Synthesis of Methionine], Chemische Berichte (1950), 83, 265-8).

The subsequently schematized compounds, 3,6-di-(2-vinyl)-2, 5-diketopiperazine and 3,6-di(2-bromoethyl)-2,5-diketopiperazine are likewise chemical precursors

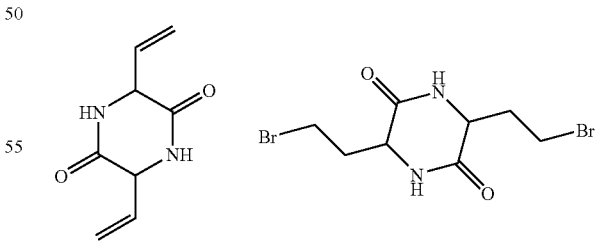

through which, according to Snyder and Chiddix ("Non-Markovnikov addition in reactions of 3,6-divinyl-2, 5-diketopiperazine", Journal of the American Chemical Society (1944), 66, 1002-4) the pathway to D,L-methionine passes. However, here also homoserine is not used.

In particular, the abovementioned objects are achieved by a method according to Claim 1. Expedient forms and modifications of the inventive method are brought under protection in the subclaims referred back to Claim 1.

By the means that a method is used for production of L-methionine, D-methionine or any desired mixtures of L- and D-methionine which starts from homoserine and in which L-homoserine, D-homoserine or corresponding mixtures of L- and D-homoserine of the formula I below

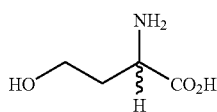
(I)

are converted to methionine by chemical transformation, without passing through any of the intermediates N-carbamoylhomoserine, 4-(2-bromoethyl)hydantoin and 4-(2-methylthioethyl)hydantoin (formulae A-C),

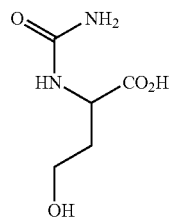
(A)

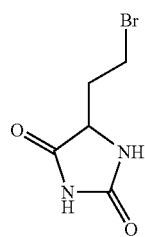
(B)

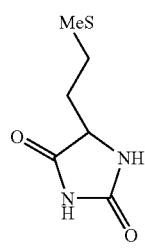
(C)

the disadvantages of the said purely chemical or direct biotechnological methods are successfully overcome.

These disadvantages are overcome, in particular, when the L-homoserine used has been produced via fermentation. It is already known that L-homoserine can be produced by fermentation of microorganisms, in particular bacteria of the family Enterobacteriaceae or coryneform bacteria, with carbon sources such as, for example, sucrose, glucose, fructose and glycerol or mixtures thereof and customary nitrogen sources such as, for example, ammonia being used.

Examples of the microbial production of L-homoserine in which Enterobacteriaceae, in particular *Escherichia coli*, are used, can be found in U.S. Pat. No. 6,303,348, U.S. Pat. No. 6,887,691 or U.S. Pat. No. 6,960,455 or EP 1217076 A1.

Examples of the microbial production of L-homoserine in which coryneform bacteria, in particular *Corynebacterium glutamicum*, are used, can be found in U.S. Pat. No. 3,189,526 or U.S. Pat. No. 3,598,701.

By using L-homoserine obtained by fermentation, the said relatively hazardous raw materials acrolein and prussic acid are successfully avoided.

However, it can also be advantageous to mix L-homoserine obtained by fermentation with racemic D,L-homoserine produced classically by the chemical route and to use a resulting mixture of D- and L-homoserine for the chemical transformation, from which at the end then corresponding mixtures of D- and L-methionine result. This can be advantageous, especially, when D-/L-homoserine is to be utilized as residue of chemical production processes of D-/L-homoserine production. Pure D-homoserine can also be used. This can be advantageous, in particular, when D-homoserine is to be utilized as residue from the separation of D-/L-homoserine racemate. The use of pure D-homoserine, however, is generally only advantageous when D-methionine is to be produced specifically.

By use of L-homoserine obtained by fermentation, it is possible, in contrast, to arrive directly at L-methionine and in fact with the use according to the invention of chemical method steps which do not impair the L configuration. In the case of exclusive use of L-homoserine, ultimately a pure L-methionine is produced which can be used directly for pharmaceutical and food uses and is distinguished in animal nutrition by higher bioefficiency compared with conventional D,L-methionine. This aspect of the method of the invention is generally of greatest benefit.

In a preferred method, use is made of an L-homoserine-containing solid product which was produced from an L-homoserine-containing fermentation broth by removal of water. This has the advantage that byproducts of fermentation can first be separated off in the L-methionine stage in the last purification step, and thus purification expenditure can be saved. If appropriate, byproducts and/or accompanying substances of fermentation can also remain in the end product if they do not interfere with the subsequent reaction or are even desired in the end product. This is the case, in particular, if they themselves have nutritious properties and L-methionine is used for feed production. Such nutritionally active compounds can be, for example, further amino acids or proteins.

Accordingly, the invention also relates to a mixed product of L-methionine and byproducts and/or accompanying substances of the production of L-homoserine by fermentation.

The L-homoserine-containing fermentation broth is expediently produced by culturing an L-homoserine-excreting microorganism in a suitable nutrient medium.

As microorganism, use is preferably made of bacteria, in particular bacteria of the genus *Corynebacterium* or *Escherichia*.

It has furthermore proved to be advantageous when the concentration of the L-homoserine in the fermentation broth is at least 1 g/l.

Surprisingly, it has been found that the chemical transformation of L- and/or D-homoserine can be carried out directly using methylmercaptan (MeSH) if appropriate in the presence of an acid catalyst. This has the great advantage that a single chemical step leads directly to the end product L-methionine. Methylmercaptan can be used here in great excesses and unconsumed methylmercaptan can subsequently readily be separated off and recycled, since, in contrast to the amino acid, it is a compound gaseous at room temperature.

Here, it has proved advantageous to use 1 to 100 mol equivalents, preferably 1 to 50 mol equivalents, of MeSH.

To accelerate the reaction and to increase the yield, it has also proved advantageous when use is made of an acid catalyst selected from the group consisting of Brönstedt acids having a $pK_a$ of $\leq 3$.

Such acids are, for example, HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkylsulphonic acid, $C_6$-$C_{10}$-arylsulphonic acid, trifluoromethanesulphonic acid, trifluoroacetic acid, or a copolymer of tetrafluoroethylene and perfluoro-3,6-dioxo-4-methyl-7-octenesulphonic acid (Nafion). Nafion as solid catalyst has the advantage, in particular, that it can readily be separated off from the reaction mixture after the reaction and be recycled.

It can likewise be advantageous when use is made of a Lewis acid catalyst. Here, mention may be made of, in particular, Lewis acid catalysts having at least one low-molecular-weight Lewis acid selected from the group $AlCl_3$, $ZnCl_2$, $BF_3 \cdot OEt_2$, $SnCl_2$, $FeCl_3$.

Also, strongly acidic ion-exchange resins which likewise can be recovered particularly readily, have proved advantageous here, in particular an optionally substituted, for example by divinylbenzene, crosslinked polystyrenesulphonic acid resin.

However, heterogeneous acid catalysts from the group zeolite, montmorrillonite and ($WO_3$- and $Cs_2O$)-containing aluminium oxide can also be used according to the invention. Among the said aluminium oxides, preference is given to those having 5-15% $WO_3$ and 5-15% $Cs_2O$ content.

Expediently, the reaction is carried out in solution and/or in suspension in the presence of water and/or an organic solvent. If the reaction is carried out in the presence of water, it can be expedient to proceed directly from an L-homoserine-containing aqueous fermentation solution, which is optionally freed from solid fractions, since in this manner advantageously, further work-up steps can be omitted. However, an aqueous crude L-homoserine can also be correspondingly advantageously used.

For instance, according to the invention, use can be made of water and/or at least one low-molecular-weight organic solvent selected from the group consisting of $C_3$ to $C_6$ ketones, preferably methyl isobutyl ketone (MIBK) or acetone, straight-chain or branched $C_1$ to $C_4$ alcohols, $C_4$ to $C_{10}$ carboxylic esters, preferably ethyl or butyl acetate, $C_3$ to $C_6$ carboxamides, preferably DMF or dimethylacetamide, $C_6$ to $C_{10}$ aromatics, preferably toluene, and $C_3$ to $C_7$ cyclic carbonates, preferably ethylene carbonate, propylene carbonate, butylene carbonate. However, methylmercaptan, used in corresponding excesses, can also act as solvent or at least as cosolvent.

According to another preferred embodiment of the invention, a method for the chemical transformation of L- and/or D-homoserine to methionine can also be carried out in such a manner that, in a first step, by introduction of a leaving group Y on the $C_4$ atom of homoserine, a compound of the formula II

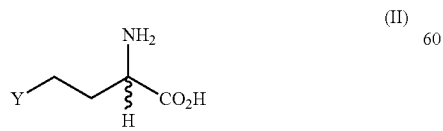

(II)

is produced, where Y is halogen(=chlorine, bromine or iodine), sulphonyloxy(=p-toluenesulphonyloxy [pTsO], $C_6H_5SO_3$, $H_3CSO_3$, $H_5C_2SO_3$ or $CF_3SO_2$), sulphate ($OSO_3H$) or phosphate ($OPO_3H$), and compound II is then reacted in a second step with MeSH to give L-methionine, D-methionine or a corresponding mixture of L- and D-methionine.

Introduction of the leaving group Y proceeds advantageously, when Y=halogen, in the first step correspondingly by reaction of the homoserine with $PCl_5$, $PCl_3$, $BBr_3$, $PJ_3$, $POCl_3$, $SOCl_2$ or $SOBr_2$.

When Y=sulphonyloxy, introduction of the leaving group Y in the first step proceeds correspondingly and advantageously by reaction with p-toluenesulphonyl chloride (p-TsCl), $C_6H_5SO_2Cl$, $H_3CSO_2Cl$, $H_5C_2SO_2Cl$ or $CF_3SO_2Cl$.

When, in contrast, Y=sulphate, for introduction of the leaving group Y, in the first step typically use is correspondingly made of $SO_3$, $H_2SO_4$ or oleum, and when Y=phosphate, preferably use is made of polyphosphoric acid to introduce Y.

After activation of the homoserine by introducing the corresponding leaving group Y in the 4 position, in a next step, the Me-S group may be particularly readily introduced by substitution of Y.

This substitution is advantageously carried out by reacting the compound of the formula II with MeSH in the presence of a basic or acid catalyst.

Suitable basic catalysts are, in particular, NaOH, KOH, pyridine, trimethylamine, triethylamine or an acetate, carbonate or hydrogencarbonate of the alkali metals or alkaline earth metals, alkali metal being lithium, sodium, potassium, rubidium or caesium and alkaline earth metal being magnesium, calcium or barium.

Suitable acid catalysts are, in particular, HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkyl-sulphonic acid, $C_6$-$C_{10}$-arylsulphonic acid, trifluoromethanesulphonic acid, trifluoroacetic acid, or a copolymer of tetrafluoroethylene and perfluoro-3, 6-di-oxo-4-methyl-7-octenesulphonic acid (Nafion) is used.

The reaction is preferably carried out in the presence of an organic solvent and/or water.

As organic solvent, use is preferably made of a low-molecular-weight organic solvent selected from the group consisting of $C_3$ to $C_6$ ketones, preferably methyl isobutyl ketone (MIBK) or acetone, straight-chain or branched $C_1$ to $C_4$ alcohols, $C_4$ to $C_{10}$ carboxylic esters, preferably ethyl or butyl acetate, $C_3$ to $C_6$ carboxamides, preferably DMF or dimethylacetamide, $C_6$ to $C_{10}$ aromatics, preferably toluene, and $C_3$ to $C_7$ cyclic carbonates, preferably ethylene carbonate, propylene carbonate or butylene carbonate.

According to a further preferred embodiment of the invention, a method for the chemical transformation of L- and/or D-homoserine to methionine can also be carried out in such a manner that, in a first step, by acid-catalysed cyclization, the corresponding 2-amino-4-butyrolactone of the formula III or salt thereof (formula IV)

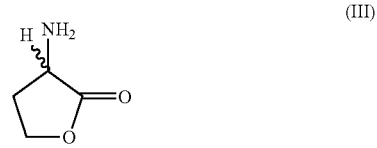

(III)

-continued

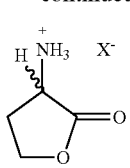
(IV)

is produced, where X is Cl, Br, I, $HSO_4$, $(SO_4)_{1/2}$, $H_2PO_4$, $(HPO_4)_{1/2}$, $(PO_4)_{1/3}$ or R'—$SO_3$ (where R'=methyl, ethyl, phenyl, tosyl), which is then reacted in a second step with MeSH to give L-methionine, D-methionine or a corresponding mixture of L- and D-methionine. In particular, the salt is a stable intermediate which can be temporarily stored or else transported, which is a not inconsiderable advantage.

Suitable acid catalysts are acids selected from the group consisting of Brönstedt acids having a $pK_a$ of $\leq 3$.

Preferably, as acid catalyst, use is made here of HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkylsulphonic acid, $C_6$-$C_{10}$-arylsulphonic acid, trifluoromethanesulphonic acid, trifluoroacetic acid or a copolymer of tetrafluoroethylene and perfluoro-3,6-dioxo-4-methyl-7-octenesulphonic acid (Nafion).

Likewise, strongly acidic ion-exchange resins are suitable as acid catalyst and in this case in particular optionally substituted, preferably by divinylbenzene, crosslinked polystyrenesulphonic acid resins.

Use can also be made of heterogeneous acid catalysts from the group ($WO_3$- and $Cs_2O$)-containing aluminium oxide, zeolite and montmorrillonite according to the invention. Among the said aluminium oxides, preference is given to those having 5-15% $WO_3$ content and 5-15% $Cs_2O$ content.

Likewise, use can be made of Lewis acid catalysts and, in particular, low-molecular-weight Lewis acids selected from the group $AlCl_3$, $ZnCl_2$, $BF_3 \cdot OEt_2$, $SnCl_2$, $FeCl_3$, which are available and inexpensive.

According to a further preferred embodiment of the invention, a method for the chemical transformation of homoserine to methionine can also be designed in such a manner that the following steps are carried out:

a) N-acylation of L- and/or D-homoserine using an acylating agent to give N-acyl-L- and/or D-homo-serine of the formula V,

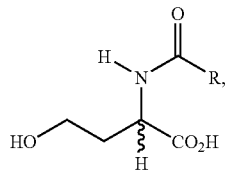
(V)

where R=hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl or $C_1$- to $C_4$-alkyloxycarbonyl, preferably tert-butyl-oxycarbonyl, or methyloxycarbonyl, b) reaction of the N-acylhomoserine V obtained in step a) with MeSH in the presence of a basic or acid catalyst to give N-acylmethionine of the formula VI

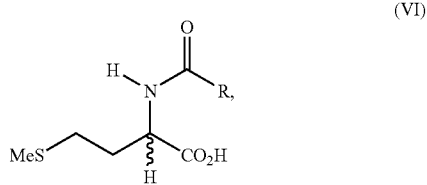
(VI)

c) hydrolysis of the N-acyl-L— and/or D-methionine obtained in step b) to give the corresponding methionine.

Depending on the exact choice of reaction conditions, in step a) either the corresponding O-acylhomoserine is primarily formed which is subsequently rearranged to form the N-acylhomoserine V, or V is formed directly in one stage.

For the acylation in step a), preferably use is made of an acylating agent of the general formula R—CO—$X^1$, where $X^1$ can be $R^1COO$, $OR^2$ ($R^2$=methyl or ethyl), Cl, Br, and R and $R^1$ can be identical or different and are hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl, or $C_1$- to $C_4$-alkyloxycarbonyl, preferably tert-butyloxycarbonyl, or methyloxycarbonyl.

As basic catalyst in step b), use can be made of NaOH, KOH, pyridine, trimethylamine, triethylamine, or an acetate, carbonate or hydrogencarbonate of the alkali metals or alkaline earth metals, where alkali metal is lithium, sodium, potassium, rubidium or caesium, and alkaline earth metal is magnesium, calcium or barium.

Suitable acid catalysts for step b) are, in particular, HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkylsulphonic acid, $C_6$-$C_{10}$-arylsulphonic acid, trifluoromethanesulphonic acid, trifluoroacetic acid, or a copolymer of tetrafluoroethylene and perfluoro-3,6-dioxo-4-methyl-7-octenesulphonic acid (Nafion).

According to a further preferred embodiment of the invention, a method for the chemical transformation of homoserine to methionine can also be designed in such a manner that the following steps are carried out:

a) N-acylation of the L- and/or D-homoserine using an acylating agent to give the N-acyl-L- and/or D-homoserine of the formula V

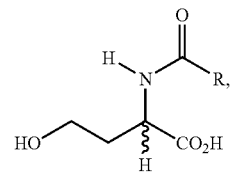
(V)

where R is hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl or $C_1$- to $C_4$-alkyloxycarbonyl, preferably tert-butyloxycarbonyl, or methyloxycarbonyl, b) conversion of the compound V obtained in step a) by introduction of a leaving group Y on the C4 atom into a compound of the formula VI

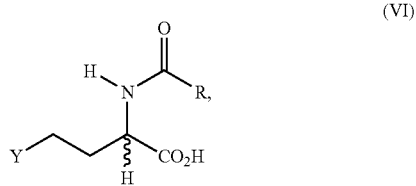

where Y is halogen(=chlorine, bromine or iodine), sulphonyloxy(=pTsO, $C_6H_5SO_3$, $H_3CSO_3$ or $H_5C_2SO_3$), sulphate ($OSO_3H$) or phosphate ($OPO_3H$), c) reaction of the compound VI obtained in step b) with MeSH in the presence of a basic or acid catalyst to give N-acyl-L-methionine, N-acyl-D-methionine or a corresponding mixture of N-acyl-L- and/or D-methionine of the formula VII

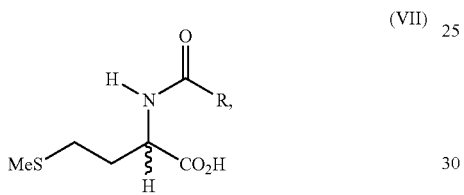

d) hydrolysis of the N-acyl-L- and/or D-methionine VII obtained in step c) to give L- and/or D-methionine.

The compound V is formed, depending on exact choice of the reaction conditions, either by rearrangement of the O-acylhomoserine primarily formed to give N-acylhomoserine, or by a combination of in-situ lactonization and acylation with subsequent ring opening.

For the acylation in step a), use is preferably made of an acylating agent of the general formula R—CO—$X^1$, where $X^1$=$R^1$COO, $OR^2$ ($R^2$=methyl or ethyl), Cl or Br and R and $R^1$ can be identical or different and are hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl or $C_1$- to $C_4$-alkyloxycarbonyl, preferably tert-butyloxycarbonyl, or methyloxycarbonyl.

The introduction of the leaving group Y proceeds advantageously, when Y=halogen, in the first step correspondingly by reaction of the homoserine with $PCl_3$, $BBr_3$, $PI_3$, $SOCl_2$ or $SOBr_2$.

When Y=sulphonyloxy, the introduction of the leaving group Y in the first step proceeds correspondingly and advantageously by reaction with p-toluenesulphonyl chloride (p-TsCl), $C_6H_5SO_2Cl$, $H_3CSO_2Cl$, $H_5C_2SO_2Cl$ or $CF_3SO_2Cl$. When, in contrast, Y=sulphate, for the introduction of the leaving group Y, in the first step typically use is correspondingly made of $SO_3$, $H_2SO_4$ or oleum. When Y=phosphate ($OPO_3H$), for the introduction of the leaving group Y, use is made in the first step typically of polyphosphoric acid.

After activation of the N-acylhomoserine by introduction of the corresponding leaving group Y in the 4 position, it is possible to introduce the Me-S group particularly readily in a next step via substitution of Y.

Suitable basic catalysts in step c) are, in particular, NaOH, KOH, pyridine, trimethylamine, triethylamine, or an acetate, carbonate or hydrogencarbonate of the alkali metals or alkaline earth metals, where alkali metal is lithium, sodium, potassium, rubidium or caesium and alkaline earth metal is magnesium, calcium or barium.

Suitable acid catalysts in step c) are, in particular, HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkylsulphonic acid, $C_6$-$C_{10}$-arylsulphonic acid, trifluoromethanesulphonic acid, trifluoroacetic acid, or a copolymer of tetrafluoroethylene and perfluoro-3,6-dioxo-4-methyl-7-octenesulphonic acid (Nafion).

According to a further preferred embodiment of the invention, a method for the chemical transformation of L- and/or D-homoserine to methionine can also be designed in such a manner that the following steps are carried out:

a) N-acylation and cyclization of the L- and/or D-homoserine using an acylating agent to give the N-acyl-L- and/or D-homoserine lactone of the formula VIII

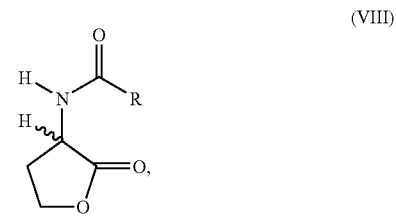

where R is hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl or $C_1$- to $C_4$-alkyloxycarbonyl, preferably tert-butyl-oxycarbonyl, or methyloxycarbonyl, b) reaction of the N-acylhomoserine lactone obtained in step a) with MeSH in the presence of a basic or acid catalyst to give the corresponding N-acyl-methionine of the formula VII

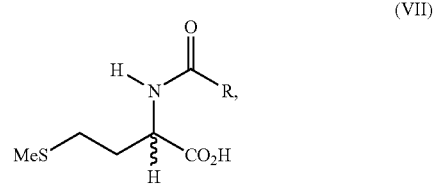

c) hydrolysis of the N-acyl-L- and/or D-methionine obtained in step b) to give the corresponding methionine at temperatures of >95° C.

For the acylation in step a), preferably use is made of an acylating agent of the general formula R—CO—$X^1$, where $X^1$=$R^1$COO, $OR^2$ ($R^2$=methyl or ethyl), Cl or Br, and R and $R^1$ can be identical or different and are hydrogen, methyl, ethyl, n-propyl, isopropyl, n-butyl, sec-butyl, tert-butyl, phenyl, mono-, di- or trihaloalkyl, where halogen=F or Cl, preferably $CF_3$ or $CCl_3$, benzyloxycarbonyl or $C_1$- to $C_4$-alkyloxycarbonyl, preferably tert-butyloxycarbonyl or methyloxycarbonyl. The N-acetylation in step a) proceeds either by rearrangement of O-acylhomoserine primarily formed to give the N-acylhomoserine with subsequent ring closure, or by a combination of in-situ lactonization and direct N-acylation.

Furthermore, in the acylation in step a), as solvent, preferably use is made of a carboxylic acid RCOOH or $R^1$COOH, where R or $R^1$ have the meaning given above, if appropriate in the presence of a further cosolvent from the group consisting of $C_3$ to $C_6$ ketones, preferably MIBK or acetone, $C_4$ to $C_{10}$ carboxylic esters, preferably ethyl or butyl acetate, $C_3$ to $C_6$ carboxamides, preferably DMF or dimethylacetamide, $C_6$ to $C_{10}$ aromatics, preferably toluene, and $C_3$ to $C_7$ cyclic carbonates, preferably ethylene carbonate, propylene carbonate or butylene carbonate.

As basic catalysts in step a), use is preferably made of pyridine derivatives, preferably dimethylaminopyridine (DMAP), or carbonyldiimidazole.

Step a) is carried out preferably at temperatures of 20 to 100° C., in particular at 50 to 90° C.

As basic catalyst in step b), preferably use is made of a catalyst which is selected from the group consisting of tetraalkylammonium hydroxides having a maximum of 48 carbon atoms, hydroxides, carbonates, hydrogen-carbonates, acetates of alkali metals or alkaline earth metals, where alkali metal is lithium, sodium, potassium, rubidium or caesium and alkaline earth metal is magnesium, calcium or barium, tertiary amines having a maximum of 36 carbon atoms and 1 to 4 nitrogen atoms, tetra($C_1$-$C_4$-alkyl)guanidine, bicyclic amines, preferably DBU (1,8-diazobicyclo[5.4.0]undec-7-ene) and TBD (1,5,7-triazabicyclo[4.4.0]dec-5-ene), pyridine and strongly alkaline ion-exchange resins.

Other preferably used basic catalysts in step b) are trialkylamines of the general formula $NR^3R^4R^5$, where $R^3$, $R^4$ and $R^5$ can be identical or different and are a linear or branched $C_1$- to $C_{12}$-alkyl radical, preferably methyl, ethyl, n-propyl, isopropyl, n-butyl or sec-butyl.

Very particularly preferred basic catalysts are N(methyl)$_3$, N(methyl)$_2$(ethyl), N(methyl)(ethyl)$_2$, N(ethyl)$_3$, N(n-propyl)$_3$, N(ethyl)(isopropyl)$_2$ or N(n-butyl)$_3$, but also diazabicyclooctane (DABCO), DBU, TBD, hexamethylenetetramine, tetramethylethylenediamine or tetramethylguanidine.

Likewise, particularly preferably, as basic catalysts, use is made of $R^3R^4R^5R^6$N-hydroxide, Li—, Na—, K—, Rb—, Cs-hydroxide, Mg—, Ca—, Ba-hydroxide, where $R^3$, $R^4$, $R^5$ and $R^6$ can be identical or different and are a linear or branched $C_1$- to $C_{12}$-alkyl radical, preferably methyl, ethyl, n-propyl, isopropyl, n-butyl or sec-butyl.

As particularly preferred basic catalysts, use is also made of $R^7R^8NR^9$-substituted crosslinked polystyrene resins, where $R^7$, $R^8$ and $R^9$ can be identical or different and are a linear or optionally branched $C_1$- to $C_4$-alkyl radical, preferably methyl, ethyl, n-propyl, n-butyl.

To achieve a rapid and as complete as possible sequence of the reaction in step b), use is made of 1 to 20 mol equivalents of base, calculated as hydroxide or N equivalent, preferably 1 to 10 mol equivalents of base.

If in step b), however, an acid catalyst is used, then it is advantageous to make use of an acid catalyst selected from the group consisting of Brönstedt acids having a $pK_a$ of $\leq 3$, or Lewis acids.

Preferably, as acid catalysts, use is made of HCl, HBr, HI, $H_2SO_4$, alkali metal $HSO_4$, $H_3PO_4$, alkali metal $H_2PO_4$, where alkali metal is lithium, sodium, potassium, rubidium or caesium, polyphosphoric acid, $C_1$-$C_{12}$-alkyl-sulphonic acid, $C_6$-$C_{10}$-arylsulphonic acid, trifluoromethanesulphonic acid, trifluoroacetic acid or a copolymer of tetrafluoroethylene and perfluoro-3,6-dioxo-4-methyl-7-octenesulphonic acid (Nafion).

However, as acid catalysts, use can also be made of strongly acidic ion-exchange resins which can readily be separated off after reaction is complete.

In this case use is preferably made of optionally substituted, preferably by divinylbenzene, crosslinked polystyrenesulphonic acid resins.

Use can also be made of heterogeneous acid catalysts from the group ($WO_3$- and $Cs_2O$)-containing aluminium oxide, zeolite and montmorrillonite. Among the said aluminium oxides, those having 5-15% $WO_3$ and 5-15% $Cs_2O$ content are preferred.

Also, use is advantageously made of Lewis acid catalysts.

As Lewis acid, use is preferably made of a low-molecular-weight Lewis acid selected from the group $AlCl_3$, $ZnCl_2$, $BF_3 \cdot OEt_2$, $SnCl_2$, $FeCl_3$.

It is also advantageous if the reaction in step b) is carried out in solution and/or in suspension in an organic solvent.

As solvent, use can be made of water and/or at least one low-molecular-weight organic solvent selected from the group consisting of $C_3$ to $C_6$ ketones, preferably MIBK or acetone, straight-chain or branched $C_1$ to $C_4$ alcohols, $C_4$ to $C_{10}$ carboxylic esters, preferably ethyl or butyl acetate, $C_3$ to $C_6$ carboxamides, preferably DMF or dimethylacetamide, $C_6$ to $C_{10}$ aromatics, preferably toluene, and $C_3$ to $C_7$ cyclic carbonates, preferably ethylene carbonate, propylene carbonate or butylene carbonate.

The hydrolysis in step c) can be carried out in aqueous solution and/or suspension.

In addition, however, it can also be advantageous if use is made additionally of at least one low-molecular-weight organic solvent which is selected from the group consisting of $C_3$ to $C_6$ ketones, preferably MIBK or acetone, straight-chain or branched $C_1$ to $C_4$ alcohols, $C_4$ to $C_{10}$ carboxylic esters, preferably ethyl or butyl acetate, $C_3$ to $C_6$ carboxamides, preferably DMF or dimethylacetamide, $C_6$ to $C_{10}$ aromatics, preferably toluene, and $C_3$ to $C_7$ cyclic carbonates, preferably ethylene carbonate, propylene carbonate or butylene carbonate.

The reaction in step c) is generally carried out at a temperature of 90 to 180° C., preferably at 100 to 160° C., in particular at 120 to 150° C., very particularly preferably at 130 to 140° C.

To accelerate the hydrolysis reaction in step c), the procedure can be carried out in addition in the presence of an acid, basic or Lewis acid catalyst, or a combination of acid and Lewis acid catalyst.

A methionine process which comprises an inventive combination of biotechnological and chemical steps has in total more advantages compared with a conventional process, in particular with respect to the mentioned requirement for a more economic, more reliable process which in addition should supply L-methionine.

Firstly, the use of sugar instead of propene (or acrolein) makes it possible to design the methionine production more economically, firstly from the point of view of current raw material costs, and secondly owing to the independence on continuously increasing costs for crude oil achieved.

Secondly, the sugar being used is a renewable raw material, so that here a valuable contribution to conservation of resources is achieved. In addition, sugar is far less dangerous than the industrial intermediates acrolein and prussic acid, so that substitution of sugar for these raw materials as starting material significantly reduces the risk potential of a production process and thus increases safety.

Thirdly, the combination of a fermentation step which makes possible the enantiospecific production of L-homoserine, makes possible, using suitable comparatively mild chemical method steps, the conversion of L-homoserine to L-methionine without racemization and in this manner leads to enantiomerically pure L-methionine. As mentioned, L-methionine has a higher bioavailability compared with currently produced D,L-methionine.

Fourthly, the production of enantiomerically pure L-methionine using a combined production process of the type described above permits the problems mentioned at the outset to be overcome elegantly, which problems are associated with production of L-methionine in a purely biotechnological way.

The inventive examples hereinafter serve for more detailed explanation of the invention without restricting the invention in any way, however.

Direct reaction of L-homoserine to give L-methionine

EXAMPLE 1

Reaction with a heterogeneous catalyst (7-10% $WO_3$/7-10% $Cs_2O$ on $Al_2O_3$ support—manufacturer—Degussa).

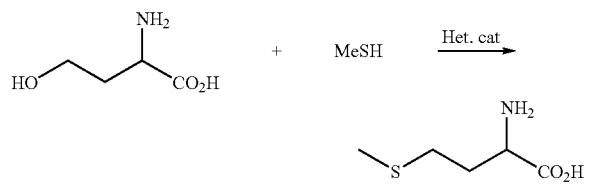

L-Homoserine (biotechnologically produced) and the finely ground heterogeneous catalyst were charged into the autoclave and MeSH was added as liquid. The autoclave was subsequently heated to 140° C. over 2.5 h. After expansion and removal of MeSH, the system was flushed with a 20% aqueous NaOH solution. The subsequent filtration and HPLC analysis gave a yield of 3% of theory of L-methionine.

In comparison: A similar attempt using a pure $Al_2O_3$ support gave only traces of methionine.

EXAMPLE 2

Reaction with isopropylthiol (iPrSH) and acid/Lewis acid (Does not come Under the Claims)

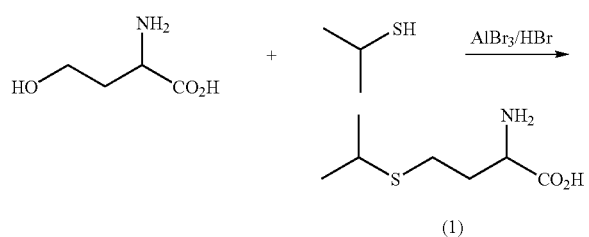

iPrSH (20 ml) was treated slowly with gaseous HBr. Subsequently L-homoserine (10 mmol) was added and the mixture was stirred for 10 minutes. Thereafter, $AlCl_3$ (40 mmol) was added and the reaction mixture was stirred for 4 h at room temperature. The reaction mixture was quenched using $H_2O$/HCl and then made basic with NaOH. After filtering off $Al(OH)_3$ by suction the filtrate solution was concentrated to dryness and analysed by HPLC. Yield of (1)=8.2%.

Activation of L-homoserine at the C-4 atom and reaction to give L-methionine

EXAMPLE 3

Activation by sulphate with subsequent nucleophilic substitution by NaSMe

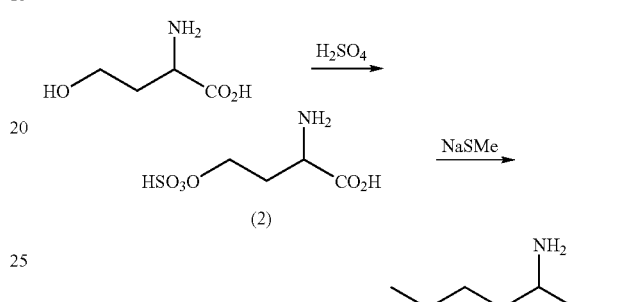

L-Homoserine (19.4 mmol) was admixed with concentrated $H_2SO_4$ (10 ml) with cooling. The resultant reaction mixture was stirred in the course of 30 minutes until the homoserine was dissolved. Subsequently the solution was allowed to stand for 3 hours at room temperature. Thereafter the reaction solution was added to 800 ml of diethyl ether cooled to −78° C., stirred well and the supernatant solution was decanted off. The solid was washed 3 times each time with 200 ml of diethyl ether at −78° C. After filtering off the whitish-yellow solid by suction, it was dried for 2 hours in an oil-pump vacuum. Yield of sulphate ester (2): 88.0%.

The sulphate ester (19 mmol) was dissolved in DMSO (20 ml) and admixed with NaSMe (50 mmol). This reaction solution was stirred at 80° C. and analysed after 90 minutes by HPLC-L-methionine yield: 19.6%. Repetition of the experiment in N-methylpyrrolidone (NMP) as solvent gave 33.6% L-methionine after 10 minutes.

Cyclization of L-homoserine and further reaction to give L-methionine

EXAMPLE 4

Production of 2-amino-4-butyrolactone hydrochloride salt

Activation by lactone formation with subsequent nucleophilic substitution by MeSH

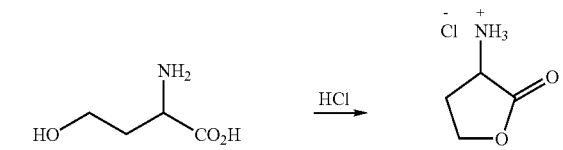

L-Homoserine (0.84 mol) was admixed with 600 ml of concentrated HCl (6.1 mol). The solution was stirred for about 15 minutes until everything had dissolved, and subsequently the water was removed under vacuum over the course of 1.5 hours. The residue was dried. Yield: 99% of 2-amino-4-butyrolactone hydrochloride salt.

EXAMPLE 5

Reaction of 2-amino-4-butyrolactone hydrochloride salt to give L-methionine

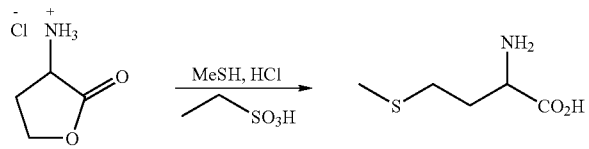

The 2-amino-4-butyrolactone hydrochloride salt (22 mmol) was charged into the autoclave in HCl-saturated ethanesulphonic acid (0.2 mol) and MeSH (0.83 mol) was added to this mixture in liquid form. Subsequently the autoclave was sealed and heated for 5 hours at 70° C. After expansion and cooling, the reaction solution was analysed by HPLC. The L-methionine yield was 21%.

EXAMPLE 6

Reaction of 2-amino-4-butyrolactone hydrobromide Salt to give L-methionine

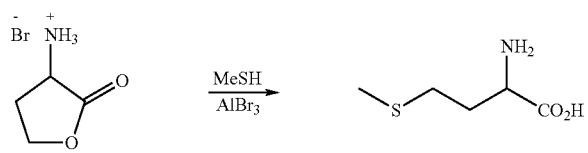

In a high-pressure autoclave, aluminium bromide (75 mmol) was carefully added to MeSH (50 ml). Subsequently, the bromide salt of the aminolactone (obtained from Aldrich) (25 mmol) was added. The autoclave was shaken for 1 hour at room temperature and thereafter for 2 hours at 40° C. The autoclave was cooled and expanded. After removal of the MeSH, the residue was quenched with water and the pH made basic using NaOH. The resultant precipitate was removed by filtration. The methionine yield was 33%.

EXAMPLE 7

Reaction of 2-amino-4-butyrolactone hydrochloride salt to sive 2-amino-4-methylthiobutyric acid

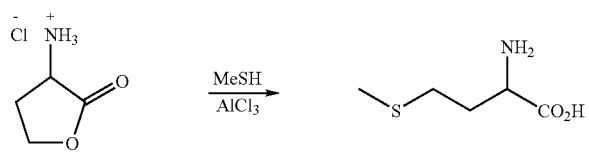

The chloride salt of the aminolactone (10 mmol) and also AlCl$_3$ (30 mmol) were charged into an autoclave and slowly admixed with MeSH (30 ml) and stirred.

Subsequently the mixture was stirred for 71 hours at room temperature. After quenching the reaction mixture with water, the yield of 2-amino-4-methylthiobutyric acid was determined by HPLC as 27%.

EXAMPLE 8

Reaction of 2-amino-4-butyrolactone hydrochloride salt to give 2-amino-4-isopropyl-thiobutyric acid (does not come under the patent claims)

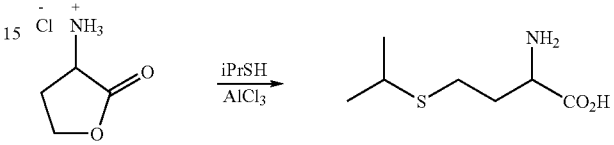

i-Propylthiol (iPrSH, 20 ml) was admixed with AlCl$_3$ (30 mmol) and stirred. Subsequently the chloride salt of the aminolactone (10 mmol) was added and the mixture was stirred for 24 hours at room temperature. After quenching the reaction mixture with water, the yield of 2-amino-4-isopropylthiobutyric acid was determined as 77% by HPLC.

EXAMPLE 9

Reaction of 2-amino-4-butyrolactone hydrochloride salt to give L-methionine

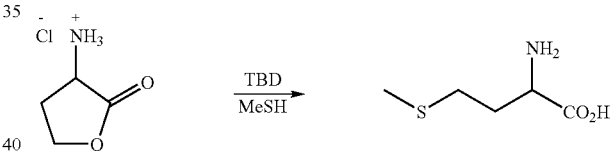

The 2-amino-4-butyrolactone hydrochloride salt (70 mmol) and TBD (1,5,7-triazabicyclo[4.4.0]dec-5-ene) (140 mmol) were charged into the autoclave and liquid MeSH was added. The sealed autoclave was heated to 70° C. over 2.5 hours. Subsequently the autoclave was gently cooled and expanded. The MeSH was removed and the residue analysed by HPLC. The L-methionine yield was 21%.

EXAMPLE 10

Cyclization of L-homoserine and N-acylation to give N-acyl-2-amino-4-butyrolactone and further reaction to give N-acyl-L-methionine (precursor of L-methionine)

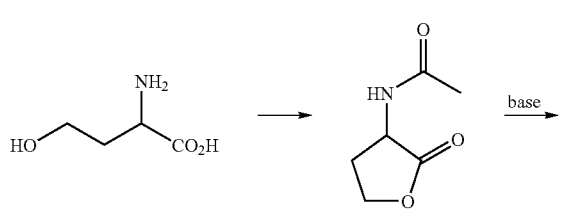

-continued

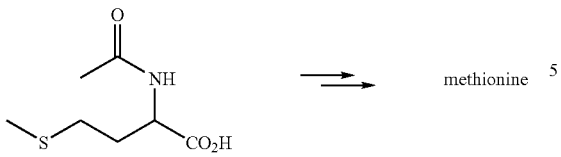 → methionine

L-Homoserine (2 mol) was suspended in 900 ml of acetic anhydride and admixed with a spatula tip full of dimethylaminopyridine (DMAP). It was slowly heated to 60° C. After approximately 1 hour, the temperature rapidly increased to 100° C. Subsequently the reaction mixture was stirred at 80° C. for 90 minutes and concentrated to dryness under vacuum. The resultant yellow oil was taken up in isopropanol (600 ml) and allowed to stand overnight at 0° C. The resultant crystals were filtered off, washed with cold isopropanol and dried under vacuum. The yield was 60% N-acetyl-2-amino-4-butyrolactone isolated, the purity 99% (according to HPLC).

Subsequently the N-acetyl-2-aminobutyrolactone (1 eq) was reacted with various bases in MeSH to give N-acetyl-methionine. A mixture of N-acetylaminolactone, base and MeSH (14 eq) was heated in a sealed autoclave. After cooling, expansion and removal of MeSH, the remaining oil was analysed by HPLC. Further details and the yield of N-acetyl-L-methionine achieved are listed in the table below:

| Base/Case a) to e) | Equivalent with respect to starting material | Temperature (° C.) | Time (h) | Yield of N-acetyl-L-met (%) |
|---|---|---|---|---|
| a) NMe$_3$ | 14 | 140 | 2.5 | 24.5% |
| b) NEt$_3$ | 14 | 140 | 7 | 19% |
| c) TMG* | 1 | 70 | 2.5 | 30.8% |
| d) TMG* | 10 | 70 | 2.5 | 57.8% |
| e) TBD** | 1 | 70 | 2.5 | 88.0% |

*Tetramethylguanidine,
**1,5,7-Triazabicyclo[4.4.0]dec-5-ene

What is claimed is:

1. A method for producing L-methionine, D-methionine or a mixture of L— and D-methionine starting from homoserine, comprising converting L-homoserine, D-homoserine or mixtures of L- and D-homoserine of the formula I:

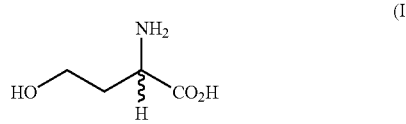

(I)

to methionine by chemical transformation, without passing through any of the intermediates N-carbamoylhomoserine, 4—(2-bromoethyl)hydantoin and 4—(2-methyl-thioethyl) hydantoin; wherein the chemical transformation of L—and/or D-homoserine is carried out in a manner that comprises:

a) using an acylating agent to produce N-acyl-L—and/or D-homoserine lactone of the formula VIII:

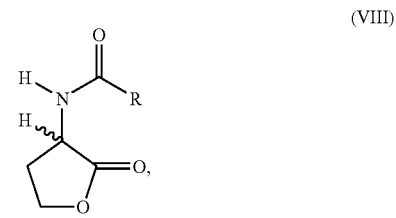

(VIII)

where R is hydrogen, methyl, ethyl, n-propyl, isopropyl, n-butyl, sec-butyl, tertbutyl, phenyl, mono-, di- or trihaloalkyl, where halogen=F or Cl, $CF_3$ or $CCl_3$, benzyloxycarbonyl or $C_1$— to $C_4$-alkyloxycarbonyl, b) reacting the N-acylhomoserine lactone obtained in step a) with MeSH in the presence of a basic or acid catalyst to give N-acylmethionine of formula VII:

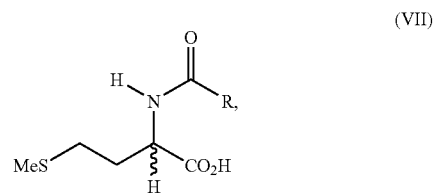

(VII)

c) hydrolyzing the N-acylmethionine obtained in step b) at temperatures of >95° C. to give methionine.

2. The method of claim 1, wherein said method is used to produce L-methionine from L-homoserine.

3. The method of claim 1, wherein said method is used to produce D-methionine from D-homoserine.

4. The method of claim 1, wherein R is hydrogen.

5. The method of claim 1, wherein R is methyl, ethyl or n-propyl.

6. The method of claim 1, wherein, in step a), said acylating agent is of the general formula R—CO—$X^1$, where $X^1$ can be $R^1COO$, $OR^2$ ($R^2$ =methyl or ethyl), Cl, Br, and R and $R^1$ can be identical or different and are selected from hydrogen, methyl, ethyl, n-propyl, isopropyl, n-butyl, sec-butyl, tert-butyl, phenyl, mono-, di- or trihaloalkyl, where halogen=F or Cl, $CF_3$ or $CCl_3$, benzyloxycarbonyl, or $C_1$- to $C_4$- alkyloxycarbonyl, preferably tert-butyloxycarbonyl, or methyloxycarbonyl.

7. The method of claim 6, wherein R and $R^1$ are hydrogen.

8. The method of claim 6, wherein R and $R^1$ are selected from the group consisting of methyl, ethyl, n-propyl.

9. The method of claim 6, wherein $X^1$ is $R^1COO$.

10. The method of claim 6, wherein $X^1$ is $OR^2$.

11. The method of claim 1, wherein, the reaction in step b) is carried out in the presence of a basic catalyst selected from the group consisting of: NaOH; KOH; pyridine; trimethylamine; triethylamine; or an acetate, carbonate or hydrogencarbonate of an alkali metal or alkaline earth metal; tertiary amines having a maximum of 36 carbon atoms and 1 to 4 nitrogen atoms, tetra($C_1$—$C_4$-alkyl)guanidine, bicyclic amines, preferably DBU (1,8-diazobicyclo[5.4.0]undec-7-ene) and TBD (1,5,7-triazabicyclo[4.4.0]dec-5-ene), and pyridine.

12. The method of claim 1, wherein, the reaction in step b) is carried out in the presence of a strongly alkaline ion-exchange resin.

13. The method of claim 1, wherein, the reaction in step b) is carried out in the presence of a Brönstedt acid selected from the group consisting of: HCl, HBr, HI, $H_2SO_4$, alkali metal $HSO_4$, $H_3PO_4$, alkali metal $H_2PO_4$, where alkali metal is lithium, sodium, potassium, rubidium or cesium, polyphosphoric acid, $C_1$—$C_{12}$-alkylsulphonic acid, $C_6$—$C_{10}$-arylsulphonic acid, trifluoromethanesulphonic acid, trifluoroacetic acid, or a copolymer of tetrafluoroethylene and perfluoro-3,6-dioxo-4-methyl-7-octenesulphonic acid (Nafion).

14. The method of claim 1, wherein, the reaction in step b) is carried out in the presence of a Lewis acid selected from the group consisting of: $AlCl_3$, $ZnCl_2$, $BF_3 \cdot OEt_2$, $SnCl_2$, and $FeCl_3$.

15. The method of claim 1, wherein the reaction in step b) is carried out in the presence of a strongly acidic ion-exchange resin.

16. The method of claim 1, wherein, the reaction in step b) is carried out in the presence of a heterogeneous acid catalyst selected from the group consisting of:

($WO_3$- and $Cs_2O$)-containing aluminium oxide, zeolite and montmorrillonite.

17. The method of claim 1, wherein the reaction in step b) is carried out in solution and/or in suspension in an organic solvent.

18. The method claim 1, wherein said the reaction in step b) is carried out in a solution and/or suspension in the presence of water and/or an organic solvent selected from the group consisting of: $C_3$ to $C_6$ ketones; straight-chain or branched $C_1$ to $C_4$ alcohols; $C_4$ to $C_{10}$ carboxylic esters; $C_3$ to $C_6$ carboxamides; $C_6$ to $C_{10}$ aromatics; and $C_3$ to $C_7$ cyclic carbonates.

19. The method of claim 1, wherein said method utilizes only homoserine having an L configuration and produced by fermenting bacteria of the genus Corynebacterium or Escherichia.

20. The method of claim 1, wherein said method utilizes only homoserine having a D configuration and produced by fermenting bacteria of the genus Corynebacterium or Escherichia.

* * * * *